US009077009B2

(12) United States Patent
Babes-Dornea et al.

(10) Patent No.: US 9,077,009 B2
(45) Date of Patent: Jul. 7, 2015

(54) FUEL CELL ELEMENT ELECTRODE INCLUDING LAYERS WITH VARYING HYDROPHOBICITY

(75) Inventors: Elena Babes-Dornea, Pierrefonds (CA); Yves Grincourt, Ottawa (CA)

(73) Assignee: General Electric Company, Schenectady, NY (US)

( * ) Notice: Subject to any disclaimer, the term of this patent is extended or adjusted under 35 U.S.C. 154(b) by 1563 days.

(21) Appl. No.: 12/190,038

(22) Filed: Aug. 12, 2008

(65) Prior Publication Data
US 2010/0040935 A1     Feb. 18, 2010

(51) Int. Cl.
| G01N 27/407 | (2006.01) |
|---|---|
| H01M 8/08 | (2006.01) |
| H01M 4/04 | (2006.01) |
| H01M 4/86 | (2006.01) |
| H01M 4/90 | (2006.01) |
| H01M 4/92 | (2006.01) |
| H01M 8/02 | (2006.01) |

(52) U.S. Cl.
CPC ............ *H01M 8/08* (2013.01); *G01N 27/4075* (2013.01); *H01M 4/0471* (2013.01); *H01M 4/8657* (2013.01); *H01M 4/90* (2013.01); *H01M 4/921* (2013.01); *H01M 8/0234* (2013.01); *H01M 8/0245* (2013.01); *H01M 2300/0085* (2013.01); *Y02E 60/50* (2013.01)

(58) Field of Classification Search
CPC H01M 4/8642; H01M 4/8803; H01M 4/8821
See application file for complete search history.

(56) References Cited

U.S. PATENT DOCUMENTS

| 5,863,395 | A | * | 1/1999 | Mah et al. ...................... 204/252 |
|---|---|---|---|---|
| 6,099,984 | A | * | 8/2000 | Rock ............................... 429/492 |
| 6,218,035 | B1 | * | 4/2001 | Fuglevand et al. ............. 429/480 |
| 6,277,513 | B1 | * | 8/2001 | Swathirajan et al. .......... 429/519 |
| 6,350,539 | B1 | * | 2/2002 | Wood et al. .................... 429/450 |
| 6,436,257 | B1 | * | 8/2002 | Babas-Dornea et al. ...... 204/415 |
| 6,436,357 | B1 | * | 8/2002 | Frieze et al. ................... 422/300 |
| 6,446,027 | B1 | * | 9/2002 | O'Keeffe et al. .............. 702/183 |
| 6,506,296 | B2 | | 1/2003 | Babes-Dornea et al. |
| 6,753,108 | B1 | * | 6/2004 | Hampden-Smith et al. ... 429/406 |
| 7,582,196 | B2 | * | 9/2009 | Babes-Dornea et al. ...... 204/400 |
| 2004/0185325 | A1 | * | 9/2004 | Faguy et al. ..................... 429/44 |
| 2007/0193885 | A1 | * | 8/2007 | Benicewicz et al. ........... 205/637 |
| 2008/0032181 | A1 | | 2/2008 | Yamamoto |

FOREIGN PATENT DOCUMENTS

| JP | 2006012476 A | 1/2006 |
|---|---|---|
| JP | 2007213865 | 8/2007 |
| JP | 2008060002 | 3/2008 |

OTHER PUBLICATIONS

Japanese Patent Application Serial No. 2009185428, Office Action dated Oct. 1, 2013.

\* cited by examiner

*Primary Examiner* — Maria J Laios
(74) *Attorney, Agent, or Firm* — Parks Wood LLC

(57) ABSTRACT

An electrode for a fuel cell element including a hydrophobic graphite support layer; a semi-hydrophobic electro-catalyst layer including an electro-catalytically active material in a carbon substrate and a polytretrofluorethylene (PTFE) content having a first concentration; and a hydrophilic electro-catalyst layer including an electro-catalytically active material in a carbon substrate and having a PTFE content having a second concentration that is less than the first concentration.

18 Claims, 3 Drawing Sheets

FUEL CELL ELEMENT ELECTRODE INCLUDING LAYERS WITH VARYING HYDROPHOBICITY

BACKGROUND OF THE INVENTION

The invention relates to a fuel cell element or sensor for the measurement of gas content in gas streams. More particularly, it relates to an electrode for such a fuel cell element and a fuel cell element including the electrode.

Industrial uses of gases such as hydrogen or acetylene require sensors for monitoring leaks and for measuring concentrations. One such device is sold under the trade name Hydran and is devoted primarily to continuous monitoring of slowly variable hydrogen concentrations. The performance of fuel cell elements is dependent on the properties of the electrodes used in the element. The electrodes in the Hydran sensor include two similar circular electrodes compressed on a polypropylene spacer having a central circular aperture filled with an electrolyte. The electrodes are cut by punching from larger electrode sheets. To meet the requirements for power fuel cell applications, the electrodes are designed to obtain maximum power at high current while maintaining minimum polarization. Fuel cell elements for use in a sensor for sensing certain gases such as hydrogen, however, require electrodes working at very low current densities with maximum concentration polarization.

BRIEF DESCRIPTION OF THE INVENTION

An electrode for a fuel cell element including a hydrophobic graphite support layer; a semi-hydrophobic electro-catalyst layer including an electro-catalytically active material in a carbon substrate and a polytretrofluorethylene (PTFE) content having a first concentration; and a hydrophilic electro-catalyst layer including an electro-catalytically active material in a carbon substrate and having a PTFE content having a second concentration that is less than the first concentration.

A first aspect of the disclosure provides an electrode, the electrode comprising: a hydrophobic graphite support layer; a semi-hydrophobic electro-catalyst layer including an electro-catalytically active material in a carbon substrate and a polytretrofluorethylene (PTFE) content having a first concentration; and a hydrophilic electro-catalyst layer including an electro-catalytically active material in a carbon substrate and having a PTFE content having a second concentration that is less than the first concentration.

A second aspect of the disclosure provides a fuel cell element comprising: a first electrode; a second electrode; a gel electrolyte positioned between the first and second electrode; at least one of the first and second electrodes including: a hydrophobic graphite support layer, a semi-hydrophobic electro-catalyst layer including an electro-catalytically active material in a carbon substrate and a polytretrofluorethylene (PTFE) content having a first concentration; and a hydrophilic electro-catalyst layer including an electro-catalytically active material in a carbon substrate and having a PTFE content having a second concentration that is less than the first concentration; an air side element supplying an oxygen containing gas to one of the electrodes; a gas side element supplying a gas mixture to the other of the electrodes; a wire contact coupled to each electrode; and a signal measuring means coupled to the wire contacts for determining a gas content of the gas mixture.

These and other aspects, advantages and salient features of the invention will become apparent from the following detailed description, which, when taken in conjunction with the annexed drawings, where like parts are designated by like reference characters throughout the drawings, disclose embodiments of the invention.

DETAILED DESCRIPTION OF THE INVENTION

Figure 1:
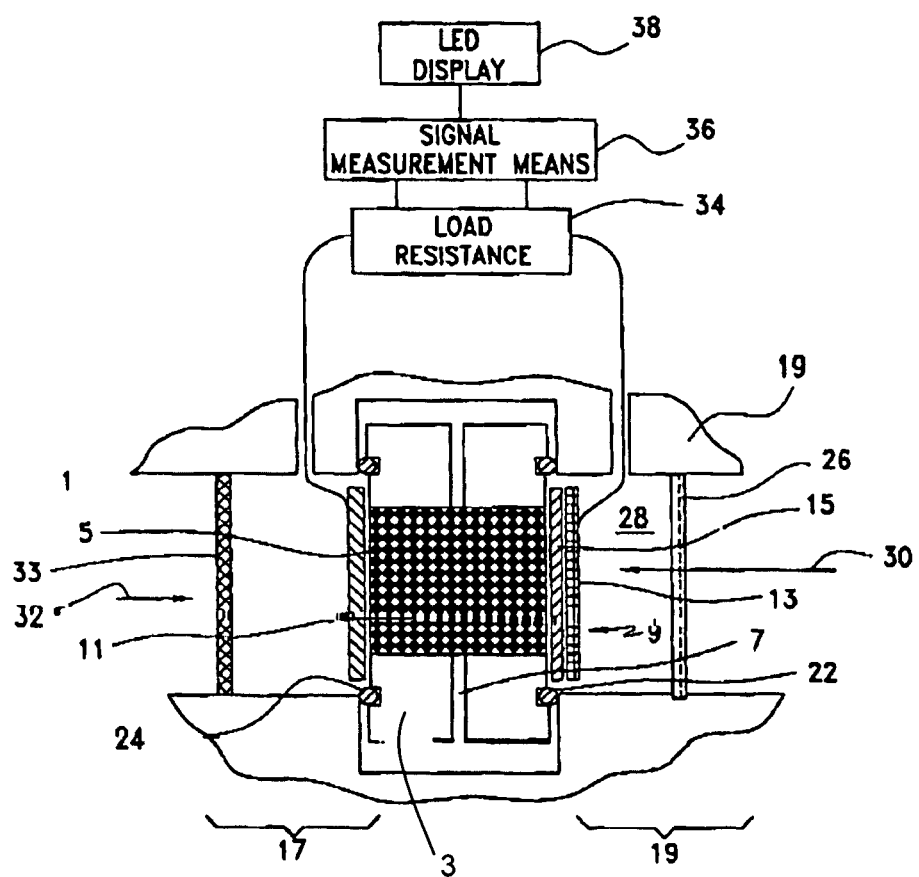
FIG. 1 is a schematic illustration of an example system or apparatus for monitoring gas exploiting a sensor device having a fuel cell element electrode of the present invention.

FIG. 1 shows, in schematic fashion, an illustrative system for monitoring a gas such as hydrogen or acetylene in a dielectric fluid. The system comprises a fuel cell element 1 including at least one electrode 11 in accordance with embodiments of the present invention. Fuel cell element 1 comprises an annular or ring-shaped support member 3, e.g., of polypropylene. Support member 3 defines a central electrolyte chamber which is filled with a suitable acidic gel electrolyte 5, e.g., of sulfuric acid ($H_2SO_4$). Support member 3 has a number of gel expansion holes, one of which is designated by the reference numeral 7.

As may be seen from FIG. 1, fuel cell element 1 is supported in a fluid tight (i.e. gas tight) fashion in a housing component. The housing component has an air side element 17 and a gas side element 19. Fuel cell element 1 may be supported in a fluid tight (i.e., gas tight) fashion in the housing component by means of the flexible O-ring seals 22, and 24. O-ring seals 22, 24 as may be appreciated from FIG. 1 are seated in annular ring grooves.

Air side element 17 and gas side element 19 each define a respective channel for delivering a gas mixture containing the gas mixture including a gas to be sensed to first electrode 9 and an oxygen containing gas (e.g., air) to second electrode 11. If the gas is to be monitored is in a reservoir containing a dielectric fluid (e.g., a liquid or a gas), then as seen in the embodiment shown in FIG. 1, gas side element 19 also is provided with a gas extraction membrane 26 disposed in the channel thereof. Gas extraction membrane 26 may be a polymeric membrane which is permeable to the particular gas, e.g., acetylene (as well as other gases), but impermeable to the dielectric fluid. Although not shown gas side element 19 may, for example, also have means (e.g., an outer threaded projection) for facilitating the attachment of the fuel cell element 1 to a valve means of the reservoir. Gas extraction membrane 26 has an outer side for contact with the dielectric fluid (e.g., dielectric oil) and an inner side which helps define a gas extraction chamber 28 between it and electrode 9. As may be appreciated a gas such as acetylene (and possibly one or more other gases) in the dielectric fluid will pass through gas extraction membrane 26 in the direction of the arrow 30 into the gas extraction chamber 28 to first electrode 9 and an oxygen containing gas such as air will pass in the direction of arrow 32 to second electrode 11. The system may include an oxygen (e.g., air) permeable membrane 33 for allowing oxygen from air to pass to second electrode 11.

Gas extraction membrane 26 is to be chosen keeping the following in mind: it should preferably be able to perform the extraction of the sensed gas (e.g., hydrogen or acetylene) dissolved in dielectric fluid (e.g., oil) at a suitable rate to be measured by the sensing element; it preferably should have a high permeability to the sensed gas and a low permeability to the other gases such as, in the case of acetylene, hydrogen, ethylene, carbon monoxide and other hydrocarbons which may be in the dielectric fluid; it should be impermeable to the dielectric fluid; etc. The gas extraction polymeric membrane may, for example, be of polyethylene, polytetrafluoroethylene (PTFE) (or Teflon™), polypropylene, fluorosilicone and the like.

Electrodes 9, 11 of fuel cell element 1 of the system shown in FIG. 1 may be electrically connected to a suitable fixed load resistance 34 (e.g., 500 to 2200 ohms) by wire contacts. Electrode 9 is illustrated as including layers 13 and 15. Layer 15 may include a PTFE material, such as Teflon™, for instance. Layer 13 can include or instance a gold deposited layer. A suitable (known) electronic signal measuring means 36 is shown as being attached across the load resistance so as to be able to permit one to measure the voltage generated by the oxido-reduction reactions occurring at the two electrode means. Electronic signal measuring means 36 may include, for example, a microprocessor to measure the signal and calculate a gas content. Electronic signal measuring means 36 is shown as being attached to an LED (light emitting diode) display element 38 for providing a visual reading with respect to the concentration of the gas. The various electronic measure and display devices may take on any suitable or desired (known) fowl. The signal generated by fuel cell element 1 is essentially a current having an intensity proportional to the gas content in the gas sample in chamber.

Current electrodes present a number of issues such as a sensor signal being lower than an acceptance limit, signal instability or non-repeatability, a high sensor offset and poor correlation between sensor signal and gas concentration. The above-described issues are caused by, for example, acid leaks through the electrode, low electro-catalytic activity, incomplete gas reaction inside the electrode, non-uniformity of electrode structure, morphology, composition, conductance and humidification, and instability of electrode structure, morphology and humidification resulting in changes during gas reaction and in time.

Figure 2:
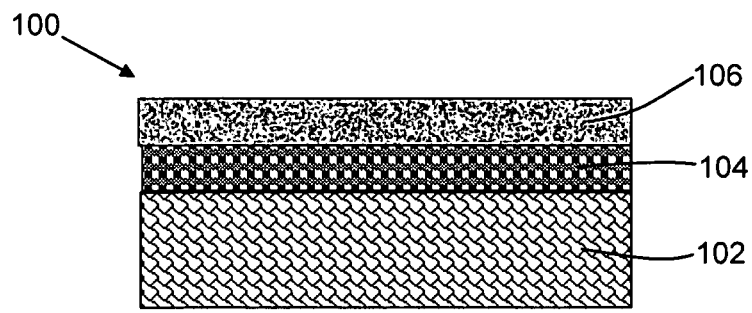
FIG. 2 is a cross-sectional view of embodiments of an electrode according to the disclosure.

Referring to FIG. 2, embodiments of an electrode 100 according to the present invention for use in a fuel cell element such as described above are illustrated. As will be described herein, electrode 100 may be employed on air side element 17 (electrode 11) (FIG. 1) and/or gas side element 19 (electrode 9) (FIG. 1). Electrode 100 may include a hydrophobic graphite support layer 102, a semi-hydrophobic electro-catalyst layer 104 and a hydrophilic electro-catalyst layer 106. Semi-hydrophobic electro-catalyst layer 104 may include an electro-catalytically active material in a carbon substrate and a polytretrofluorethylene (PTFE) content having a first concentration, and hydrophilic electro-catalyst layer 106 may include an electro-catalytically active material in a carbon substrate and a PTFE content having a second concentration, where the second concentration is less than the first concentration.

In one embodiment, hydrophobic graphite support layer 102 includes at least one layer of graphite paper having sufficient mechanical rigidity and made hydrophobic to avoid acid leaks in conditions of low gas pressure. For example, support layer 102 may include a plurality of bonded graphite paper layers such as available from Toray that have been coated with PTFE so as to make them hydrophobic.

As noted above, semi-hydrophobic electro-catalyst layer 104 may include a PTFE content having a first concentration, while hydrophilic electro-catalyst layer 106 includes a PTFE content having a second concentration that is less than the first concentration. Hence, second layer 106 is less hydrophobic than first layer 104 to allow more electrolyte absorption by the second layer. Second layer 106 faces gel electrolyte 5 (FIG. 1) and support layer 102 faces a gas phase, i.e., air side element 17 or gas side element 19. As used herein, "hydrophobic" indicates a substantial inability to absorb water (i.e., approximately 0% absorption), "semi-hydrophobic" indicates a water absorption capability of, for example, 10-50%, and "hydrophilic" indicates a water absorption capability of, for example, 60-100%, where the percentage indicates a water absorbed in material divided by weight of the dry material times 100.

Semi-hydrophobic electro-catalyst layer 104 may be formed in a number of ways. In one embodiment, the carbon substrate may include a number of carbon paper sheets such as available from Toray coated with a PTFE solution. For example, the pair of carbon paper sheets may be initially coated by spraying a diluted PTFE solution and then allowing them to dry. The carbon paper sheets may then be heated to make the carbon paper sheets hydrophobic. The electro-catalyst may be formed by mixing a powder of an electro-catalytically active material with distilled water. The electro-catalytically active material may include noble metals such as, but not limited to: platinum (Pt) and alloys thereof, ruthenium (Ru), palladium (Pd), iridium (Ir), gold (Au), vanadium (V), titanium (Ti), nickel (Ni), scandium (Sc) or rhodium (Rh). Such powders may be available from sources such as Alfa-Aesar. Isopropanol may then be added with a PTFE solution 20 to 60%, available from DuPont. The solution including PTFE may then be repeatedly sprayed onto the carbon paper sheets with the carbon paper sheets allowed to dry between each application. Subsequently, the carbon paper sheets may be annealed, and then compressed under heating to from electro-catalyst layer 104.

Hydrophilic electro-catalyst layer 106 may also be formed in a number of ways. In one embodiment, electro-catalyst layer 106 is formed by a process that includes initially coating a carbon substrate such as a pair of carbon paper sheets, such as available from Toray, with a PTFE solution. For example, the pair of carbon paper sheets may be coated by spraying a diluted PTFE solution and then allowing the sheets to dry. The carbon paper sheets may then be heated to make the carbon paper sheets hydrophobic. The electro-catalyst may be formed by mixing a powder of an electro-catalytically active material with iso-propanol and distilled water with a PTFE solution. The electro-catalytically active material may include noble metals such as, but not limited to: platinum (Pt) and alloys thereof, ruthenium (Ru), palladium (Pd), iridium (Ir), gold (Au), vanadium (V), titanium (Ti), nickel (Ni), scandium (Sc) or rhodium (Rh). Such powders may be available from sources such as Alfa-Aesar. The electro-catalytically active material on layer 106 may be the same as or different than that used on layer 104. The mixture including PTFE is heated to obtain a concentrated, buttery mixture, which is uniformly spread onto the carbon paper sheets. The spreading process may be repeated as necessary to eliminate cracks, undulations or tears. The carbon paper sheets may then be compressed and dried, as necessary, to obtain a substantially crack-free layer. Subsequently, the carbon paper sheets may be annealed to arrive at electro-catalyst layer 106.

Hydrophobic support layer 102 and electro-catalyst layers 104, 106 are combined under pressure and heat to ensure adequate adhesion to form electrode 100. Although particular embodiments of processes of forming layers 102, 104, 106 have been described, it is understood that a variety of other processes may also be employed and are considered within the scope of the invention.

Figure 3:
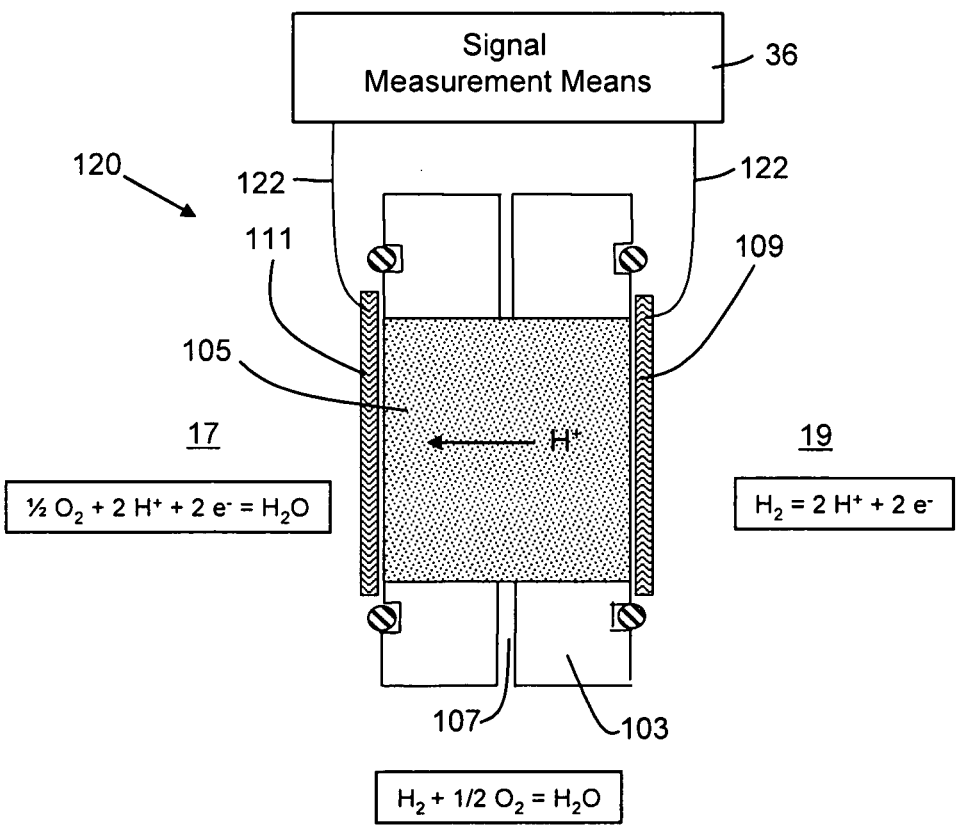
FIG. 3 is a partial cross-sectional view of one embodiment of a fuel cell element according to the disclosure.

Referring to FIG. 3, one embodiment of a fuel cell element 120 according to the disclosure is illustrated. FIG. 3 shows a partial cross-sectional view of fuel cell element 120, which would be provided with other structure as illustrated in FIG. 1. Fuel cell element 120 may include a first electrode 109 and a second electrode 111. At least one of the first and second electrodes 109, 111 includes hydrophobic graphite support layer 102 (FIG. 2), semi-hydrophobic electro-catalyst layer 104 and hydrophilic electro-catalyst layer 106, as described herein. A gel electrolyte 105 may be positioned between first and second electrodes 109, 111, which may be positioned within a support member 103 (e.g., of polypropylene) defining a central electrolyte chamber. Support member 103 has a number of gel expansion holes, one of which is designated by the reference numeral 107. An air side element 17 supplies an oxygen containing gas to electrode 111, and a gas side element 19 supplies a gas mixture to electrode 109. A wire contact 122 is provided to each electrode. A signal measuring means 36 (FIG. 1) is coupled to wire contacts 122 for determining a gas content of the gas mixture. Although not shown in FIG. 3, signal measuring means 36 may be coupled with an LED and load resistance as described relative to FIG. 1.

Fuel cell element 120 is configured to monitor hydrogen ($H_2$) gas content within gas side element 19. Oxygen in an oxygen-containing gas such as air is reduced at electrode 111, and the oxidation of hydrogen ($H_2$) occurs at electrode 109. Fuel cell element 120 is configured such that gel electrolyte 105 is in contact with both electrodes for facilitating the desired oxidation and reduction reactions at respective electrodes, i.e., they are not spaced apart from the gel electrolyte as shown in the schematic illustration of FIGS. 1, 3 and 4. The chemical reactions occurring within fuel cell element 120 are illustrated in FIG. 3. The reaction illustrated in the lowermost text box is the global reaction occurring during the sensing of hydrogen.

Figure 4:
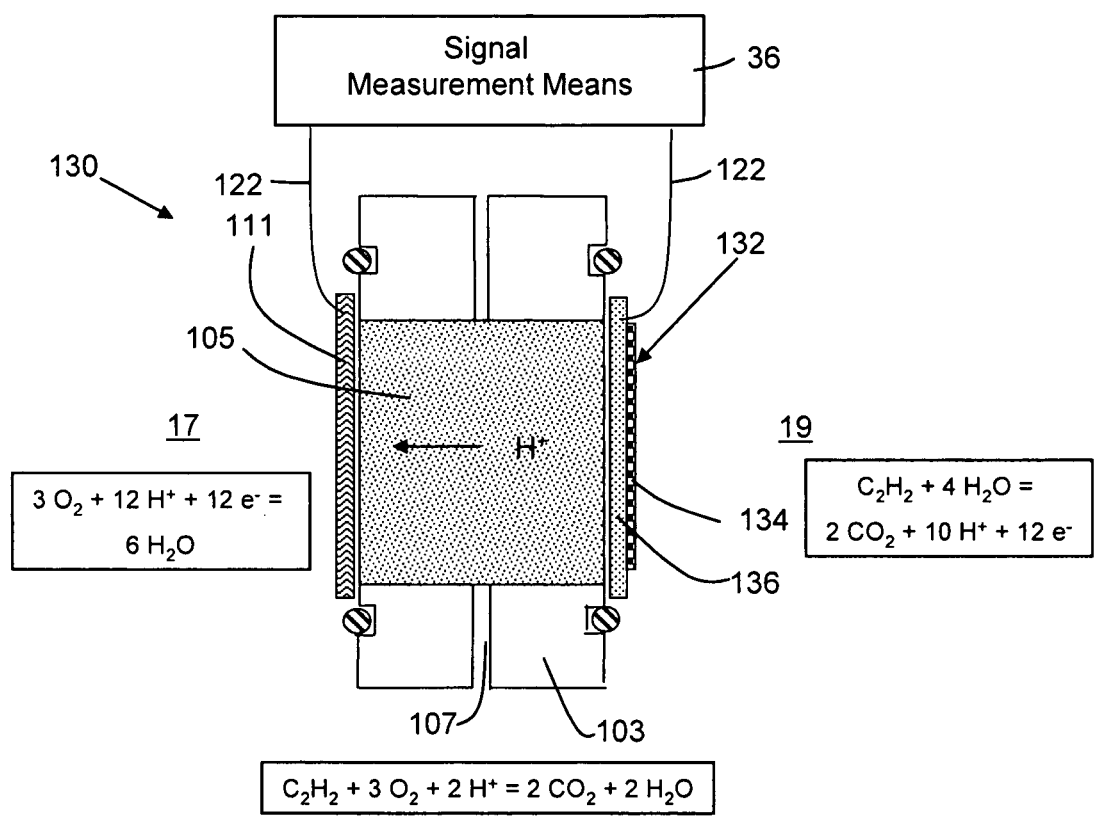
FIG. 4 is a partial cross-sectional view of an alternative embodiment of the fuel cell element.

FIG. 4 shows an alternative embodiment of a fuel cell element 130 configured for monitoring acetylene ($C_2H_2$) gas content. Fuel cell element 130 includes one electrode 111 according to the present invention used with another electrode 132 as described, for example, in U.S. Pat. No. 6,436,257. Electrode 132 includes two elements namely a porous, gas permeable gold layer 134 and an electrolyte substrate 136. Electrolyte substrate 136 includes a gold and Nafion® gas permeable layer. Nafion is a sulfonated tetrafluoroethylene copolymer available from DuPont. Oxygen in an oxygen-containing gas such as air is reduced at electrode 111, and oxidation of acetylene occurs at electrode 132. Fuel cell element 130 is configured such that gel electrolyte 105 is in contact with both electrodes for facilitating the desired oxidation and reduction reactions at respective electrodes, i.e., they are not spaced apart from the gel electrolyte as shown in the schematic illustration of FIGS. 1, 3 and 4. The chemical reactions occurring within fuel cell element 130 are illustrated in FIG. 4. The reaction in the lowermost text box occurs as the global reaction during the sensing of acetylene.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context, (e.g., includes the degree of error associated with measurement of the particular quantity). The suffix "(s)" as used herein is intended to include both the singular and the plural of the term that it modifies, thereby including one or more of that term (e.g., the metal(s) includes one or more metals).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims

What is claimed is:

1. A gas sensor electrode for measuring gas content in gas streams, the electrode comprising:
    a hydrophobic graphite support layer coated in polytetrafluoroethylene (PTFE) having a water absorption capability of approximately 0%;
    a semi-hydrophobic electro-catalyst layer, which is less hydrophobic than the hydrophobic graphite support layer and having a water absorption capability of 10% to 50% by weight, including an electro-catalytically active material in a carbon substrate and a polytetrafluoroethylene (PTFE) content having a first concentration; and
    a hydrophilic electro-catalyst layer including an electro-catalytically active material in a carbon substrate and having a PTFE content having a second concentration that is less than the first concentration and having a water absorption capability of 60% to 100%.

2. The electrode of claim 1, wherein the semi-hydrophobic electro-catalyst layer is obtained by spraying a solution including the PTFE content onto the carbon substrate.

3. The electrode of claim 1, wherein the hydrophilic electro-catalyst layer is obtained by spreading a mixture including PTFE onto the carbon substrate.

4. The electrode of claim 1, wherein the hydrophobic graphite support layer includes a graphite paper.

5. The electrode of claim 1, wherein the hydrophobic graphite support layer faces a gas phase of the electrode, and the hydrophilic electro- catalyst layer faces a gel electrolyte of the electrode.

6. The electrode of claim 1, wherein the electro-catalytically active material for the semi-hydrophobic electro-catalyst layer and the hydrophilic electro-catalyst layer is selected from the group consisting of: platinum (Pt) and alloys thereof, ruthenium (Ru), palladium (Pd), iridium (Ir), gold (Au), vanadium (V), titanium (Ti), nickel (Ni), scandium (Sc) and rhodium (Rh).

7. A gas sensor for measuring gas content in gas streams comprising:
    a first electrode;
    a second electrode;
    a gel electrolyte positioned between the first and second electrode;
    at least one of the first and second electrodes including:
        a hydrophobic graphite support layer coated in polytetrafluoroethylene (PTFE) having a water absorption capability of approximately 0%;
        a semi-hydrophobic electro-catalyst layer, which is less hydrophobic than the hydrophobic graphite support layer and having a water absorption capability of 10% to 50% by weight, including an electro-catalytically active material in a carbon substrate and a polytetrafluoroethylene (PTFE) content having a first concentration; and a hydrophilic electro-catalyst layer including an electro-catalytically active material in a carbon substrate and having a PTFE content having a second concentration that is less than the first concentration and having a water absorption capability of 60% to 100%;

an air side element supplying an oxygen containing gas to one of the electrodes;

a gas side element supplying a gas mixture to the other of the electrodes;

a wire contact coupled to each electrode; and a signal measuring means coupled to the wire contacts for determining a gas content of the gas mixture.

8. The sensor of claim 7, wherein the semi-hydrophobic electro-catalyst layer is obtained by spraying a solution including the PTFE content onto the carbon substrate.

9. The sensor of claim 7, wherein the hydrophilic electro-catalyst layer is obtained by spreading a mixture including PTFE onto the carbon substrate.

10. The sensor of claim 7, wherein the hydrophobic graphite support layer includes a graphite paper.

11. The sensor of claim 7, wherein the hydrophobic graphite support layer faces a gas phase of the sensor, and the hydrophilic electro-catalyst layer faces the gel electrolyte.

12. The sensor of claim 7, wherein both the first and second electrodes include:

the hydrophobic graphite support layer;
the semi-hydrophobic electro-catalyst layer; and the hydrophilic electro-catalyst layer.

13. The sensor of claim 12, wherein the sensor monitors hydrogen gas.

14. The sensor of claim 7, wherein one of the first and second electrodes includes the hydrophobic graphite support layer, the semi-hydrophobic electro-catalyst layer, and the hydrophilic electro-catalyst layer, and the other of the first and second electrodes includes a gold and perfluorosulfonic acid polymer gas permeable layer and a porous, gas permeable gold layer.

15. The sensor of claim 14, wherein the sensor monitors acetylene gas.

16. The sensor of claim 7, wherein the gel electrolyte includes sulfuric acid ($H_2SO_4$).

17. The sensor of claim 7, wherein the gel electrolyte is positioned within a polypropylene support.

18. The sensor of claim 7, wherein the electro-catalytically active material for the semi-hydrophobic electro-catalyst layer and the hydrophilic electro-catalyst layer is selected from the group consisting of: platinum (Pt) and alloys thereof, ruthenium (Ru), palladium (Pd), iridium (Ir), gold (Au), vanadium (V), titanium (Ti), nickel (Ni), scandium (Sc) and rhodium (Rh).

* * * * *

UNITED STATES PATENT AND TRADEMARK OFFICE
CERTIFICATE OF CORRECTION

PATENT NO. : 9,077,009 B2
APPLICATION NO. : 12/190038
DATED : July 7, 2015
INVENTOR(S) : Babes-Dornea et al.

Page 1 of 1

It is certified that error appears in the above-identified patent and that said Letters Patent is hereby corrected as shown below:

In the specification,

In Column 3, Line 13, delete "lavers" and insert -- layers --, therefor.

In Column 3, Line 15, delete "include or instance" and insert -- include, for instance, --, therefor.

In Column 3, Line 27, delete "fowl." and insert -- form. --, therefor.

In Column 3, Line 29, delete "chamber." and insert -- chamber 28. --, therefor.

Signed and Sealed this
Fifteenth Day of March, 2016

Michelle K. Lee
*Director of the United States Patent and Trademark Office*